United States Patent [19]

Komissarov et al.

[11] Patent Number: 5,187,277

[45] Date of Patent: Feb. 16, 1993

[54] DL-3-[4-[4-(2-PYRIDYL)-1-PIPERAZINYL]-BUTYL]-1,8,8-TRIMETHYL-3-AZABICY-CLO[(3,2,1]OCTANE-2,4-DIONE HAVING PSYCHOTROPIC AND ANTIEMETIC EFFECT

[76] Inventors: Igor V. Komissarov, ulitsa Artema, 100, kv.57; Vladimir I. Dulenko, prospekt Osvobozhdenia Donbassa, 2a, kv.45; Valentin N. Voschula, ulitsa Universitetskaya, 63, kv.19; Nikolai A. Kharin, ulitsa Artema, 136b, vk.99; Sergei V. Naletov, prospekt Gurova, 7, kv.33; Alexandr B. Mamonov, prospekt Iliicha, 16, kv.102, all of Donetsk, U.S.S.R.

[21] Appl. No.: 749,270

[22] Filed: Aug. 23, 1991

[30] Foreign Application Priority Data

Oct. 29, 1990 [SU] U.S.S.R. .................... 4875060

[51] Int. Cl.$^5$ ........................................... C07D 401/14
[52] U.S. Cl. ........................... 544/362; 544/231; 544/360; 546/112
[58] Field of Search ................... 544/230, 362

[56] References Cited

U.S. PATENT DOCUMENTS 3,717,634  2/1973  Wu et al. .................. 544/230
4,748,240  5/1988  Stack et al. ................ 544/295
4,892,943  1/1990  Abou-Gharbia ........... 544/234

FOREIGN PATENT DOCUMENTS 288369  5/1988  European Pat. Off. .

OTHER PUBLICATIONS

Goa et al, *Drugs*, 32, p. 114 (1986).
Boissier et al, *Arch. Int. Pharmacodyn.* 147 p. 372 (1964).
Protais et al, *Psychopharmacology*, 50, p. 1 (1976).
Dunham et al, *J. Am. Pharmacol. Sci.* 46, p. 208 (1957).
Presiosi et al, *Arch. Int. Pharmacodyn.* 298, p. 301 (1989).

*Primary Examiner*—Mukund J. Shah
*Assistant Examiner*—E. Bernhardt
*Attorney, Agent, or Firm*—Burgess, Ryan & Wayne

[57]  ABSTRACT

Disclosure is made of a compound of the formula:

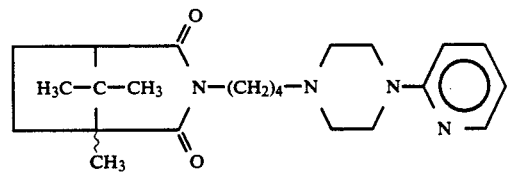

and pharmaceutically acceptable salts thereof. A salt, for instance, the dihydrochloride is usable as a compound which exhibits psychotropic and antiemetic effect.

2 Claims, No Drawings

DL-3-[4-[4-(2-PYRIDYL)-1-PIPERAZINYL]-BUTYL]-1,8,8-TRIMETHYL-3-AZABICYCLO[(3,2,1]OCTANE-2,4-DIONE HAVING PSYCHOTROPIC AND ANTIEMETIC EFFECT

BACKGROUND OF THE INVENTION

1. Field of the Invention

The present invention relates to novel, biologically active compounds, in particular, to DL-3-[4-[4-(2-pyridyl)-1-piperazinyl]-butyl]-1,8,8-trimethyl-3-azabicyclo[3,2,1]octane-2,4-dione having psychotropic and antiemetic properties.

2. Background of the Related Art

At present, widely used in medical practice are psychotropic agents which affect psychic functions, emotional state and behaviour of humans. With respect to the therapeutic effect such agents can be divided into neuroleptics, tranquilizers, antidepressants, etc. Neuroleptics, such as phenothiazine, butyrophenone and thioxanthene derivatives, which have pronounced antipsychotic properties, are used for treating psychoses, schizophrenia and other psychic diseases. As distinct from neuroleptics, tranquilizers, such as meprotane and analogous agents, benzodiazepine derivatives, are used for treating a wide range of neurotic and neurosis-like disorders reducing, first of all, emotional stress, anxiety and fear. Neuroleptics and tranquilizers produce hypnosedative and musculorelaxation effect at a different rate, which often gives an undesirable result.

The need for such agents increases the necessity for searching for a novel compounds having psychotropic properties.

Known in the art are tranquilizers such as N-(heteroarylcyclic)piperazinylalkylazaspiroalkane diones of the formula:

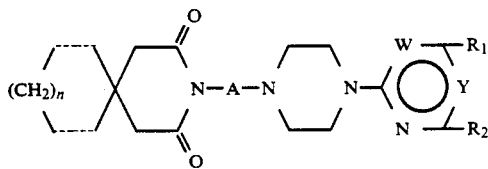

wherein A, $R_1$ and $R_2$ are alkyls, W and Y are CH or N when n is 4 or 5 (US,A, 3,717,634). One of said compounds such as 8-[4-[4-(2-pyrimidinyl)-1-piperazinyl]-butyl]-8-azaspiro[4,5]decane-7,9-dione buspirone is used as a therapeutic agent (K. Goa, A. Ward, Drugs,32, p. 114, 1986).

Described in EP 0268369 are bridged bicyclic imides of the formula:

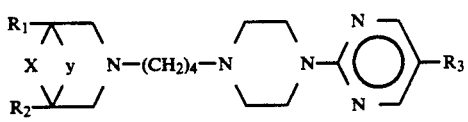

wherein
X is $CH_2$, $CH_2$-$CH_2$ or $CH_2CH_2CH_2$;
y is $CH_2$, $CH(CH_3)$, $C(CH_3)_2$, $C(CH_2)_4$, $CH_2CH_2$;
$R_1$ and $R_2$ are H or $CH_3$, and $R_3$ is H or F.
Said imides are usable as tranquilizers and antidepressants.

SUMMARY OF THE INVENTION

The object of the present invention is to broaden the range of organic compounds usable as psychotropic agents.

Said object is accomplished by providing DL-3-[4-[4-(2-pyridyl)-1-piperazinyl]-butyl]-1,8,8-trimethyl-3-azabicyclo-[3,2,1]-o ctane-2,4-dione of the formula:

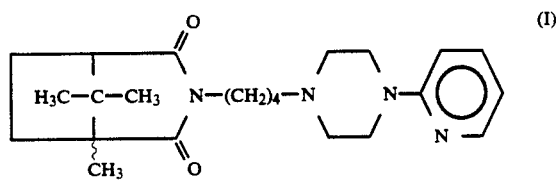

and pharmaceutically acceptable salts thereof.

The compound of the present invention shows the properties of a potential neuroleptic free of cataleptogenic (extrapyramidic) activity. Its antianxiety activity is three times as large as that of buspirone and said bicyclic imides (in a conflict situation model). The activity of compound of formula I according to the invention as demonstrated in the tests which are characteristic of neurgleptics (climbing and antiaggressive tests), was two to four times as large as that of said compounds. The antiemetic effect of the present compound is 10–100 times as large as that of all comparable compounds (haloperidol, triphthazine, metoclopramide). It can be concluded from the above that the present compound is distinguished over buspirone and a bicyclic imide by a higher anxiolytic and essentially more pronounced neuroleptic and antiemetic activities.

Compound I according to the invention is prepared by reacting DL-1,8,8-trimethyl-3-azabicyclo [3,2,1]octane-2,4-dione (DL-camphorimide) of the formula:

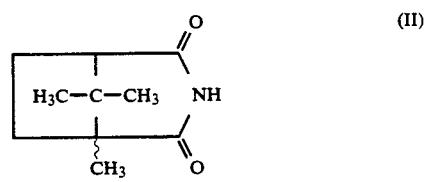

with 8-(2-pyridyl)-8-aza-5-azoniaspiro[4,5]decane bromide of the formula:

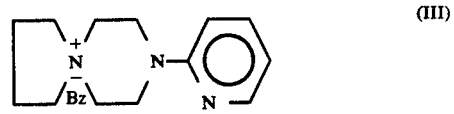

The reaction is carried out under heating, preferably, boiling, of equimolar amounts of compounds of formulae II and III until it is totally completed. The reactants are usually heated in a polar solvent selected from the group comprising n-butanol, dimethyl acetamide, N-methyl pyrrolidone, in the presence of, preferably, potassium carbonate. The reaction is performed under unhydrous conditions for 12–30 hours. The compound of formula III is prepared by reacting 1-(2-pyridyl)-piperazine of formula IV:

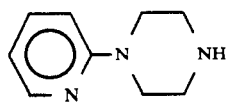

(IV)

with 1,4-dibromobutane of formula V:

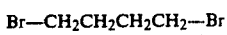

$Br-CH_2CH_2CH_2CH_2-Br$ (V).

The reaction is carried out in a polar solvent, for instance, isopropyl alcohol, in the presence of, preferably, soda ash, under heating. The reaction is continued until it is fully complete, under unhydrous conditions for 12-24 hours. Compound I according to the invention is a base and is capable of forming acid addition salts thereof. All said salts are within the scope of the present invention, however, used in pharmaceutical compositions there should be pharmaceutically acceptable salts. Usually, compound I is combined with a stoichiometric amount of a corresponding acid in an inert, polar solvent which can be anhydrous or hydrous, or partially hydrous. The resulting salt is filtered off and recrystallized from the inert solvent or dried in vacuum. Said salts comprises hydrochlorides, hydrobromides, citrates, 4-toluene sulfonates, etc.

According to the present invention, the disclosure is also made of a pharmaceutical composition (tablets, injectable solutions) comprising a pharmaceutically acceptable carrier such as dihydrochloride, and compound I as active agent.

The anxiolytic activity of dihydrochlorides of compounds I, buspirone (VI) and DL-3-[4-(2-pyrimidinyl)-1-piperazinyl]-butyl]-1,8,8-trimethyl-3azabic yclo[3,2,-1]octane-2,4-dione (VIII), as well as of diazepame, and haloperidol, was evaluated in conflict situation models (T. Klygul, V. Krivolapov. Pharmacology and Toxicology, No. 29, p. 241, 1966) and by the method of avoiding illuminated areas. The compounds were introduced intraperitoneally and orally 20-60 minutes before the beginning of the test. The minimum effective doses (MED) increasing the number of water takings and increasing the period of staying in an illuminated area by at least 50%, were determined. The neuroleptic activity was detected and measured using the "rat fight" method and the "climbing" test of mice (P. Protais et al. Psychopharmacology, 50, p. 1, 1976). The sedative activity of dihydrochlorides of compounds I, VI, VII and diazepame was evaluated by means of suppression of spontaneous locomotion and orientation behaviour (J. Boissier, P. Simon. Arch. Int. Pharmacodyn., 147, p. 372, 1964), the myorelaxation activity was evaluated by the rotating rod test (M. Dunham, T. Miya, J. Am. Pharmacol. Sci., 46, p. 208, 1957),the narcosepotentiation activity was evaluated by the increase of effect of a nonnarcotic dose of hexobarbital. The antiemetic effect on vomiting caused by apomorphine or cisplatin was studied in pigeons (P. Presiosi et al., Arch. Int. Pharmacodyn., 298, p. 301, 1989) and mongrel dogs having a weight of 6-8 kg.

Table 1 shows the tranquilizing and neuroleptic activities of dihydrochlorides of compounds I, VI, VII, diazepame, haloperidol and sulpyride.

TABLE 1

| Compound 1 | Anxiolytic activity MED, mg/kg on rats in | | | | Antiaggressive activity $ED_{50} \pm \int \bar{x}, mg/kg$ | | Antiapomorphine activity in "climbing" test $ED_{50} \pm \int \bar{x}, mg/kg$ | Hexobarbital-potentiation effect $ED_{50} \pm \int \bar{x}, mg/kg$ | |
|---|---|---|---|---|---|---|---|---|---|
| | conflict tests | | "avoiding illuminated area" tests | | | | | | |
| | i/p 2 | orally 3 | i/p 4 | orally 5 | i/p 6 | orally 7 | i/p 8 | i/p 9 | orally 10 |
| I | 1 | 3 | 1 | 10 | 7.45 ± 1.6 | 30.8 ± 4.14 | 0.7 ± 0.13 | 17.6 ± 2.9 | 12.5 ± 3.14 |
| VI | 3 | — | 3 | — | — | — | 2.6 ± 0.46 | 8.2 ± 2.4 | — |
| VII | 3 | 3 | 3 | 10 | 28.5 ± 4.2 | 81.5 ± 8.30 | 1.31 ± 0.15 | 11.9 ± 2.2 | 36.5 ± 8.11 |
| Diazepame | 1 | — | 1 | 1 | — | 5.9 ± 1.28 | — | 0.3 ± 0.1 | 0.48 ± 0.12 |
| Haloperidol | >3 | — | — | — | — | — | 0.67 ± 0.06 | — | — |
| Sulpyride | — | — | — | — | 60.6 ± 16.6 | — | 8.4 ± 1.3 | — | — |

It was found that the systematic application of dihydrochlorides of compound I according to the invention at a rate of 0.1-50 mg/kg of a body weight produces the effect which is characteristic of tranquilizers and neuroleptics, i.e. anxiolytic, antiaggressive, antiapomorphine and hexobarbital-potentiation effects.

The anxiolytic activity of compounds I, VI, VII in two anxiety models is close, however, the activity of compound I is three times as large as that of compounds VI, VII (intraperitoneally). Only the anxiolytic doses of compound I coincide with the similar doses of diazepame (when administered intraperitoneally). On the contrary, the activity of compound I which potentiates the activity of hexobarbital, is essentially lower than the activity of diazepame. It is only compound I that is comparable to haloperidol as an apomorphine antagonist in a "climbing" test.

Table 2 below shows the sedative and myorelaxation activities and toxicity of dihydrochlorides of compounds I, VI, VII and diazepame.

TABLE 2

| Compound 1 | Sedative activity $ED_{50} \pm \int \bar{x}, mg/kg$ Supression of | | Myorelaxation activity $ED_{50} \pm \int \bar{x}, mg/kg$ i/p 4 | Toxicity $DL_{50} \pm \int \bar{x}, mg/kg$ i/p 5 |
|---|---|---|---|---|
| | motor activity i/p 2 | orientation behaviour i/p 3 | | |
| I | 2.8 ± 0.7 | 3.9 ± 0.9 | 44.5 ± 10.0 | 208 ± 20 |
| VI | 8.7 ± 1.8 | 7.6 ± 1.9 | 54.2 ± 8.1 | 140 ± 20 |
| VII | 5.4 ± 2.3 | 7.7 ± 1.6 | 52.5 ± 12.0 | 211 ± 31 |
| Diazepame | 0.6 ± 0.2 | 0.6 ± 0.2 | 2.4 ± 0.2 | 110 ± 27 |

It can be concluded from Table 2 that the sedative and myorelaxation activities and toxicity of compound I are much lower than the activity and toxicity of diazepame.

Table 3 below shows the antiemetic activity of dihydrochlorides of compounds I, VII, haloperidol, trifluoperazine, metoclopramide in pigeons.

TABLE 3

| Compound 1 | Antiemetic activity, $ED_{50} \pm \int \bar{x}$, mg/kg Vomiting caused by | |
|---|---|---|
| | apomorphine, 15 mg/kg i/p 2 | cisplatin, 7.5 mg/kg i/p 3 |
| I | 0.11 ± 0.02 | 0.4 ± 0.07 |
| VII | 1.8 ± 0.4 | 4.6 ± 0.8 |
| Haloperidol | 3.4 ± 0.5 | 4.4 ± 0.9 |
| Trifluoperazine | 4.6 ± 0.8 | 5.5 ± 0.9 |
| Metoclopramide | 12.0 ± 1.7 | 9.7 ± 1.1 |

It can be seen from Table 3 that the antiemetic and antiapomorphine activities of compound I is substantially higher than those of other compounds. In dog tests, compound I applied at a rate of from 0.003 to 0.25 mg/kg prevents vomiting caused by apomorphine and cisplatin. $ED_{50}$ is 0.02±0.006 and 0.013±0.005 mg/kg of body weight, respectively.

It can be concluded from the above-stated that compound I of the present invention possesses pronounced tranquilizing, neuroleptic and antiemetic activities at a low toxicity.

DETAILED DESCRIPTION OF THE INVENTION.

The below examples illustrate the particular preparations of compound I and salts thereof.

EXAMPLE 1

8-(2-pyridyl)-8-aza-5-azoniaspiro[4,5]decane bromide (III)

A mixture of 40.8 g (0.25 mol) of 1-(2-pyridyl) piperazine (IV), 75.5 ml (134.9 g, 0.625 mol) of 1,4-dibromobutane (V) and 27.5 g (0.26 mol) of sodium carbonate was refluxed in 500 g of isopropyl alcohol for 16 hours, the hot mixture was filtered off from the salt precipitate, cooled, and the crystalline product was isolated. The additional amount of the product can be obtained by dilution of the mother liquor with a double volume of ether.

Total yield: 74.5 g (90%), mp. 197°–198° C.
Found, %: C 52.54, H 6.90, N 13.96, Br 26.60, $C_{13}H_{20}BrN_3$.
Calculated, %: C 52.36, H 6.76, N 14.09, Br 26.79.
IR spectrum, $cm^{-1}$: 1635, 1595, 1572, 1485, 1445, 1390, 1320, 1265, 1145, 985, 960, 930, 780, 740.
NMR-$^1$H spectrum ($CD_3OD$): 2.20–2.40 (4H, m, 2,3-H of spirodecane), 3.59–3.80 (8H, m, 1,4,7,9-H of spirodecane), 3.85–3.96 (4H, m, 6, 10-H of spirodecane), 6.82 (1H, td, $J_1$=6 Hz, $J_2$=2 Hz, 5-H of pyridine), 6.99 (1H, d, J=8 Hz, 3-H of pyridine), 7.87 (1H, td, $J_1$=8 Hz, $J_2$=2 Hz, 4-H of pyridine, 8.17 (1H, d, J=6 Hz, 6-H of pyridine).

EXAMPLE 2

DL-3-[4-[4-(2-pyridyl)-1-piperazinyl]-butyl]-1,8,8-trimethyl-3-azabicyclo[3,2,1]octane-2,4-dione (I).

A mixture of 4.07 g (0.0225 mol) of DL-camphorimide (II), 6.71 g (0.0225 mol) of 8-(2-pyridyl)-8-aza-5-azoniaspiro[4,5]-decane bromide (III) and 3.73 g (0.027 mol) of potassium carbonate was refluxed in 80 ml of absolute dimethylformamide for 24 hours, then the resulting mixture was cooled, filtered, and dimethylformamide was distilled off under reduced pressure. The residue was dissolved in 100 ml of 5% HCl, the resulting solution was extracted twice with 50 ml of ether to remove impurities of non-basic nature, and saturated with soda. The precipitated base was extracted with ethyl acetate, the extract was dried with potassium carbonate and purified by passing through a column packed with a neutral aluminum oxide 5 cm thick (with ethyl acetate as eluent). After the solvent was distilled off, there was obtained a free base in the form of an oil which was then crystallized. Mp. 96°–97° C.

Found, %: C 69.4, H 8.6, N 14.0, $C_{23}H_{34}N_4O_2$.
Calculated, %: C 69.3, H 8.6, N 14.1.
IR spectrum, $cm^{-1}$: 3440, 2950, 1725, 1685, 1600, 1490, 1440, 1360, 1315, 1250, 1185, 1170, 1150, 1100, 1085, 985, 960, 950, 880.

EXAMPLE 3

DL-3-[4-[4-(2-pyridyl)-1-piperazinyl]-butyl]-1,8,8-trimethyl-3-azabicyclo[3,2,1]octane-2,4-dione dihydrochloride (I).

To be converted into a dihydrochloride according to Example 2, compound I was dissolved in 50 ml of absolute ether and passed through gaseous HCl until it was saturated. The precipitated dihydrochloride was filtered off, washed with absolute ether and recrystallized from isopropyl alcohol. The yield of the pure product in the form of white crystalline powder was 9.02 g (85%). Mp. 189°–190° C.

Found, %: C 58.5, H 7.7, N 12.0, Cl 15.1, $C_{23}H_{36}N_4Cl_2O_2$.
Calculated, %: C 58.6, H 7.7, N 11.9, Cl 15.0.
IR spectrum, $cm^{-1}$: 3470, 2960, 2930, 1725, 1670, 1635, 1610, 1540, 1435, 1355, 1280, 1180.

EXAMPLE 4

DL-3-[4-[4-(2-pyridyl)-1-piperazinyl]-butyl]-1,8,8-trimethyl-3-azabicyclo[3,2,1]octane-2,4-dione (I) ditosylate.

To a solution of 0.399 g (0.001 mol) of compound I obtained according to Example 2, in 5 ml of iospropyl alcohol, there was added a solution of 0.38 g (0.002 mol) of p-toluenesulphonic acid monohydrate in 3 ml of the same solvent. The mixture was thoroughly mixed, and 40 ml of absolute ether was added thereto. The precipitated ditosylate was filtered off and dried in vacuum to yield 0.742 g (~100%) of the product. Mp. 137°–138° C.

Found, %: C 60.0, H 6.7, N 7.5, S 8.7, $C_{37}H_{50}N_4O_8S_2$.
Calculated, %: C 59.8, H 6.8, N 7.5, S 8.6.
IR spectrum, $cm^{-1}$: 3440, 2960, 1630, 1670, 1640, 1610, 1440, 1400, 1350, 1200, 1130, 1040, 1015, 820, 770, 690, 570.

EXAMPLE 5

A mixture of 1.81 g (0.01 mol) of DL-camphorimide (II), 2.98 g (0.01 mol) of 8-(2-pyridyl)-8-aza-5-azoniaspiro[4,5]decane bromide (III) and 1.66 g (0.012 mol) of potassium carbonate was refluxed for 24 hours in 150 ml of anhydrous n-butanol. The reaction mixture was treated following the procedure of Examples 2 and 3. The yield of the product was 3.06 g (65%).

EXAMPLE 6

The reaction was performed following the procedure of Example 5, except that used as a solvent was dry dimethyl acetamide (40 ml), and the mixture was refluxed for 20 hours. The yield of the product was 3.77 g (80%).

EXAMPLE 7

The reaction was performed following the procedure of Example 5, except that used as a solvent was dry N-methyl pyrrolidone (40 ml), and the mixture was refluxed for 15 hours. The yield of the product was 3.4 g (72%).

What is claimed is:

1. DL-3-[4-[4-(2-pyridyl)-1-piperazinyl]-butyl]-1,8,8-trimethyl-3-azabicyclo[3,2,1]octane-2,4-dione of the formula:

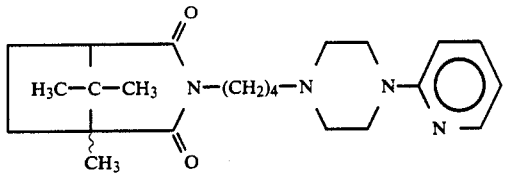

and pharmaceutically acceptable salts thereof.

2. DL-3[4-[4-(2-pyridyl)-1-piperazinyl]-butyl]-1,8,8-trimethyl-3-azabicyclo[3,2,1]oct ane-2,4-dione dihydrochloride.

* * * * *